(12) United States Patent
Haney et al.

(10) Patent No.: US 8,414,286 B2
(45) Date of Patent: Apr. 9, 2013

(54) SPACER MOLDS WITH RELEASABLE SECUREMENT

(75) Inventors: Sean Haney, North Canton, OH (US); Scott M. Sporer, Wheaton, IL (US)

(73) Assignee: Zimmer Orthopaedic Surgical Products, Inc., Dover, OH (US)

( * ) Notice: Subject to any disclaimer, the term of this patent is extended or adjusted under 35 U.S.C. 154(b) by 460 days.

(21) Appl. No.: 12/328,159

(22) Filed: Dec. 4, 2008

(65) Prior Publication Data

US 2010/0102484 A1 Apr. 29, 2010

Related U.S. Application Data

(60) Provisional application No. 61/109,355, filed on Oct. 29, 2008.

(51) Int. Cl.
*B29C 45/17* (2006.01)

(52) U.S. Cl. .................. 425/577; 264/328.7

(58) Field of Classification Search .......... 425/577, 425/451.9, DIG. 221, 56; 264/328.7
See application file for complete search history.

(56) References Cited

U.S. PATENT DOCUMENTS

| | | | |
|---|---|---|---|
| 1,520,849 A * | 12/1924 | Birnbach | 249/158 |
| 1,612,133 A * | 12/1926 | Lee | 249/158 |
| 3,596,554 A * | 8/1971 | Low et al. | 411/348 |
| 3,774,244 A | 11/1973 | Walker | |
| 3,816,855 A | 6/1974 | Saleh | |
| 3,964,106 A | 6/1976 | Hutter, Jr. et al. | |
| 4,016,606 A | 4/1977 | Murray et al. | |
| 4,059,684 A | 11/1977 | Gross et al. | |
| 4,191,740 A | 3/1980 | Heusser et al. | |
| 4,297,993 A | 11/1981 | Härle | |
| 4,373,217 A | 2/1983 | Draenert | |
| 4,610,692 A | 9/1986 | Eitenmuller et al. | |
| 4,615,705 A | 10/1986 | Scales et al. | |
| 4,717,115 A | 1/1988 | Schmitz et al. | |
| 4,749,585 A | 6/1988 | Greco et al. | |
| 4,790,740 A * | 12/1988 | Pearlman | 425/396 |
| 4,815,960 A | 3/1989 | Rudolph | |
| 4,822,365 A | 4/1989 | Walker et al. | |

(Continued)

FOREIGN PATENT DOCUMENTS

| | | |
|---|---|---|
| DE | 29703971 U1 | 7/1998 |
| EP | 0378928 A1 | 7/1990 |

(Continued)

OTHER PUBLICATIONS

PCT Search Report from related PCT/US2008/085527; Jul. 13, 2009; 17 pages.

(Continued)

*Primary Examiner* — Galen Hauth
(74) *Attorney, Agent, or Firm* — Schwegman, Lundberg & Woessner, P.A.

(57) ABSTRACT

A mold for forming a temporary prosthesis has at least two mold members at least partially separable from each other. The at least two mold members cooperatively define a generally enclosed interior cavity for forming the temporary prosthesis. The mold has a securement structure mounted on the at least two mold members for securing the at least two mold members to each other during the forming of the temporary prosthesis. The securement structure is removable from the at least two mold members by hand and without the use of a tool.

25 Claims, 12 Drawing Sheets

U.S. PATENT DOCUMENTS

| | | | |
|---|---|---|---|
| 4,843,112 A | 6/1989 | Gerhart et al. | |
| 4,853,225 A | 8/1989 | Wahlig et al. | |
| 4,882,149 A | 11/1989 | Spector | |
| 4,900,546 A | 2/1990 | Posey-Dowty et al. | |
| 4,919,666 A | 4/1990 | Buchhorn et al. | |
| 4,919,679 A | 4/1990 | Averill et al. | |
| 4,959,071 A | 9/1990 | Brown et al. | |
| 5,030,237 A | 7/1991 | Sorbie et al. | |
| 5,033,712 A | 7/1991 | Ravet | |
| 5,044,921 A * | 9/1991 | Micelli et al. | 425/451.9 |
| 5,059,209 A | 10/1991 | Jones | |
| 5,061,286 A | 10/1991 | Lyle | |
| 5,098,620 A | 3/1992 | Bradley et al. | |
| 5,106,614 A | 4/1992 | Posey-Dowty et al. | |
| 5,123,927 A | 6/1992 | Duncan et al. | |
| 5,133,771 A | 7/1992 | Duncan et al. | |
| 5,151,279 A | 9/1992 | Kimura | |
| 5,171,282 A * | 12/1992 | Pequignot | 623/20.35 |
| 5,197,986 A | 3/1993 | Mikhail | |
| 5,226,915 A | 7/1993 | Bertin | |
| 5,236,457 A | 8/1993 | Devanathan | |
| 5,286,763 A | 2/1994 | Gerhart et al. | |
| 5,501,687 A | 3/1996 | Willert et al. | |
| 5,549,684 A | 8/1996 | Amino et al. | |
| 5,681,289 A | 10/1997 | Wilcox et al. | |
| 5,693,099 A | 12/1997 | Härle | |
| 5,980,573 A | 11/1999 | Shaffner | |
| 6,155,812 A | 12/2000 | Smith et al. | |
| 6,193,493 B1 | 2/2001 | Steijer et al. | |
| 6,245,111 B1 | 6/2001 | Shaffner | |
| 6,361,731 B1 * | 3/2002 | Smith et al. | 264/271.1 |
| 6,506,217 B1 | 1/2003 | Arnett | |
| 6,540,786 B2 | 4/2003 | Chibrac et al. | |
| 6,755,563 B2 | 6/2004 | Wahlig et al. | |
| 6,787,097 B1 | 9/2004 | Homann et al. | |
| 6,821,470 B2 | 11/2004 | Gundlapalli et al. | |
| 6,887,276 B2 | 5/2005 | Gerbec et al. | |
| 6,905,582 B2 | 6/2005 | Kidd et al. | |
| 6,916,308 B2 | 7/2005 | Dixon et al. | |
| 6,942,475 B2 | 9/2005 | Ensign et al. | |
| 7,070,622 B1 | 7/2006 | Brown et al. | |
| 7,077,867 B1 | 7/2006 | Pope et al. | |
| 7,109,254 B2 | 9/2006 | Muller et al. | |
| 7,153,327 B1 | 12/2006 | Metzger | |
| 7,255,715 B2 | 8/2007 | Metzger | |
| 7,320,709 B2 | 1/2008 | Felt et al. | |
| 7,326,252 B2 | 2/2008 | Otto et al. | |
| 7,338,529 B1 | 3/2008 | Higgins | |
| 7,427,296 B2 | 9/2008 | Evans | |
| 7,429,346 B2 | 9/2008 | Engisn et al. | |
| 7,575,602 B2 | 8/2009 | Amirouche et al. | |
| 7,601,176 B2 | 10/2009 | Soffiati et al. | |
| 7,789,646 B2 | 9/2010 | Haney et al. | |
| 2002/0010431 A1 | 1/2002 | Dixon et al. | |
| 2003/0009230 A1 | 1/2003 | Gundlapalli et al. | |
| 2003/0009231 A1 | 1/2003 | Gundlapalli et al. | |
| 2003/0021180 A1 | 1/2003 | Wahlig et al. | |
| 2003/0075564 A1 | 4/2003 | Wahlig et al. | |
| 2003/0103408 A1 | 6/2003 | Foster | |
| 2004/0036189 A1 | 2/2004 | Ensign et al. | |
| 2004/0054417 A1 | 3/2004 | Soffiati et al. | |
| 2004/0066706 A1 | 4/2004 | Barker et al. | |
| 2004/0083003 A1 | 4/2004 | Wasielewski | |
| 2004/0196735 A1 | 10/2004 | Barker et al. | |
| 2004/0236424 A1 | 11/2004 | Berez et al. | |
| 2004/0236429 A1 | 11/2004 | Ensign et al. | |
| 2004/0249382 A1 | 12/2004 | Olson, Jr. et al. | |
| 2005/0033424 A1 | 2/2005 | Fell | |
| 2005/0085918 A1 | 4/2005 | Soffiati et al. | |
| 2005/0096747 A1 | 5/2005 | Tuttle et al. | |
| 2005/0107885 A1 | 5/2005 | Evans | |
| 2005/0119756 A1 | 6/2005 | Soffiati et al. | |
| 2005/0171604 A1 | 8/2005 | Michalow | |
| 2006/0004431 A1 | 1/2006 | Fuller et al. | |
| 2006/0093646 A1 | 5/2006 | Cima et al. | |
| 2006/0255512 A1 * | 11/2006 | Joyner | 264/496 |
| 2007/0100450 A1 | 5/2007 | Hodorek | |
| 2007/0100462 A1 | 5/2007 | Lang et al. | |
| 2007/0104819 A1 | 5/2007 | Ness et al. | |
| 2007/0141106 A1 | 6/2007 | Bonutti et al. | |
| 2007/0142392 A1 | 6/2007 | Murphy et al. | |
| 2007/0162144 A1 | 7/2007 | Wasielewski | |
| 2007/0213835 A1 | 9/2007 | Wimmer et al. | |
| 2007/0222114 A1 | 9/2007 | Ziran et al. | |
| 2007/0233266 A1 | 10/2007 | Williams, III et al. | |
| 2007/0270447 A1 | 11/2007 | Hunter et al. | |
| 2007/0282451 A1 | 12/2007 | Metzger et al. | |
| 2008/0027431 A1 | 1/2008 | Williams et al. | |
| 2008/0058950 A1 | 3/2008 | Leonard et al. | |
| 2008/0086210 A1 | 4/2008 | Fox | |
| 2008/0097605 A1 | 4/2008 | Pastorello | |
| 2008/0097606 A1 | 4/2008 | Cragg et al. | |
| 2008/0119931 A1 | 5/2008 | Fell et al. | |
| 2008/0133020 A1 | 6/2008 | Blackwell et al. | |
| 2008/0269909 A1 | 10/2008 | Vogt et al. | |
| 2009/0234459 A1 | 9/2009 | Sporring et al. | |
| 2009/0295035 A1 | 12/2009 | Evans | |
| 2010/0102484 A1 | 4/2010 | Haney et al. | |
| 2010/0185298 A1 | 7/2010 | Stone | |
| 2010/0292803 A1 | 11/2010 | Giori | |
| 2010/0297276 A1 | 11/2010 | Haney et al. | |
| 2011/0054481 A1 | 3/2011 | Sproul | |
| 2011/0071072 A1 | 3/2011 | Calderone et al. | |

FOREIGN PATENT DOCUMENTS

| | | |
|---|---|---|
| EP | 0602274 A1 | 6/1994 |
| EP | 0811359 A2 | 12/1997 |
| EP | 1952787 A1 | 8/2008 |
| EP | 2298696 A1 | 3/2011 |
| IT | 1278853 A1 | 3/1997 |
| JP | 02065858 A2 | 3/1990 |
| JP | 2001017454 | 1/2001 |
| JP | 2006015042 A1 | 1/2006 |
| WO | 9851240 A1 | 11/1998 |
| WO | 0003855 A1 | 1/2000 |
| WO | 0154561 A1 | 8/2001 |
| WO | WO01/76512 A1 | 10/2001 |
| WO | WO03/086241 A1 | 10/2003 |
| WO | 2005025451 A2 | 3/2005 |
| WO | WO2006/090226 A1 | 8/2006 |
| WO | 2007005667 A2 | 1/2007 |
| WO | 2007056667 A2 | 5/2007 |
| WO | 2007084878 A1 | 7/2007 |
| WO | 2007136417 A2 | 11/2007 |
| WO | 2007144667 A2 | 12/2007 |
| WO | 2008020904 A2 | 2/2008 |
| WO | 2009073781 A2 | 6/2009 |
| WO | WO2009/076168 A1 | 6/2009 |
| WO | WO2010015877 A1 | 2/2010 |

OTHER PUBLICATIONS

Goodell et al., "Preparation and Release Characteristics of Tobramycin-impregnated Polymethylmethacrylate Beads," American Journal of Hospital Pharmacy; vol. 43, Jun. 1986, p. 1454-1461.

Cohen et al., "Two-Stage Reimplantation of Septic Total Knee Arthroplasty," The Journal of Arthroplasty; vol. 3, No. 4, 1988, p. 369-377.

Booth et al., "The Results of Spacer Block Technique in Revision of Infected Total Knee Arthroplasty," Clinical Orthopaedics and Related Research; 1989, p. 57-60.

Henderson et al., "The Use of an Antibiotic-Impregnated Spacer Block for Revision of the Septic Total Knee Arthroplasty," Seminars in Arthroplasty, vol. 2, No. 1, Jan. 1991, p. 34-39.

Search Report from related PCT/US2008/085538; dated Jun. 18, 2009; 11 pages.

International Preliminary Report on Patentability mailed May 3, 2011 in related International Application No. PCT/US2008/085538.

* cited by examiner

SPACER MOLDS WITH RELEASABLE SECUREMENT

CROSS-REFERENCE TO RELATED APPLICATION

This application claims priority from U.S. Provisional Application Ser. No. 61/109,355, filed Oct. 29, 2008, the contents of which are incorporated herein by reference in their entirety.

FIELD OF THE INVENTION

The present invention is directed to molds for forming orthopedic implants and, more particularly, to molds for forming temporary spacer orthopedic implants.

BACKGROUND OF THE INVENTION

From time to time, orthopedic implants such as a knee replacement and the tissue around the implant can become infected. The infected implant is removed, and it conventionally takes four to eight weeks or more to adequately treat the infection during which time the implant site is kept immobile. This may cause unused muscles to contract and shrink the space previously occupied by the joint implant that connected articulating bones such as the space between the end of a femur and the tibia bone in the case of a knee replacement.

To prevent the shrinkage of the implant site, one treatment is to replace the infected permanent implant with a temporary implant or spacer made of an antibiotic-filled cement to fill the void. The spacer preserves the distance between the adjoining bones so that muscle cannot overly contract while the infection is being cleared from the implant site. Additionally, once positioned within the body, the antibiotic leaches out of the spacer to treat tissue near the spacer and prevent further spreading of the infection. The spacer is usually left in the void for four to eight weeks, but can be implanted for up to six months to clear the infection. Once the infection is cleared, the spacer is replaced with a new permanent implant. Ideally this type of spacer will allow some movement and preserve joint spacing, but is not usually intended to support the loads encountered by healthy bone or permanent, long term implants.

Some known spacers are pre-made and are provided to the physicians performing the surgery. This usually provides little or no opportunity for the physicians to significantly customize or modify the spacer to match the size of a patient's implant site. The pre-made spacers also cannot be easily and quickly modified to change the implant configuration. For instance, the physician may at first desire a knee implant to have a medullar stem to be placed axially into a medullary cavity in the femur or tibia but then reverse that decision upon opening the implant site. At that point, however, it may not be convenient, or even possible, to remove such a stem from a pre-made knee implant.

Other spacers are molded by the physicians by filling molds with curable cement during the surgical procedure. In these cases, when hard molds are used, substantial customization is not possible when a mold is provided in one size and configuration. Also, relatively cumbersome, time consuming, and messy procedures are used to fill the molds. For instance, such hard molds are usually filled by pouring the antibiotic filled cement into mold pieces and then placing the cement into all spaces in the mold by using a spoon or spatula. In other cases, the molds are inserted in-situ at the surgical site and the implant is made while the mold is in-situ.

Other known relatively soft silicone spacer molds are enclosed for injecting cement into the mold from a cement gun with a nozzle. To fill all of the spaces in the enclosed mold, extra time and effort by the physician is required to shift and/or rotate the nozzle of the cement gun in different directions within the mold. Thus, a spacer mold is desired that permits physicians to easily and quickly select and adjust the size and configuration of the spacer mold, even while the implant site is accessible, and efficiently and cleanly fill the spacer mold.

DETAILED DESCRIPTION

Figure 1:
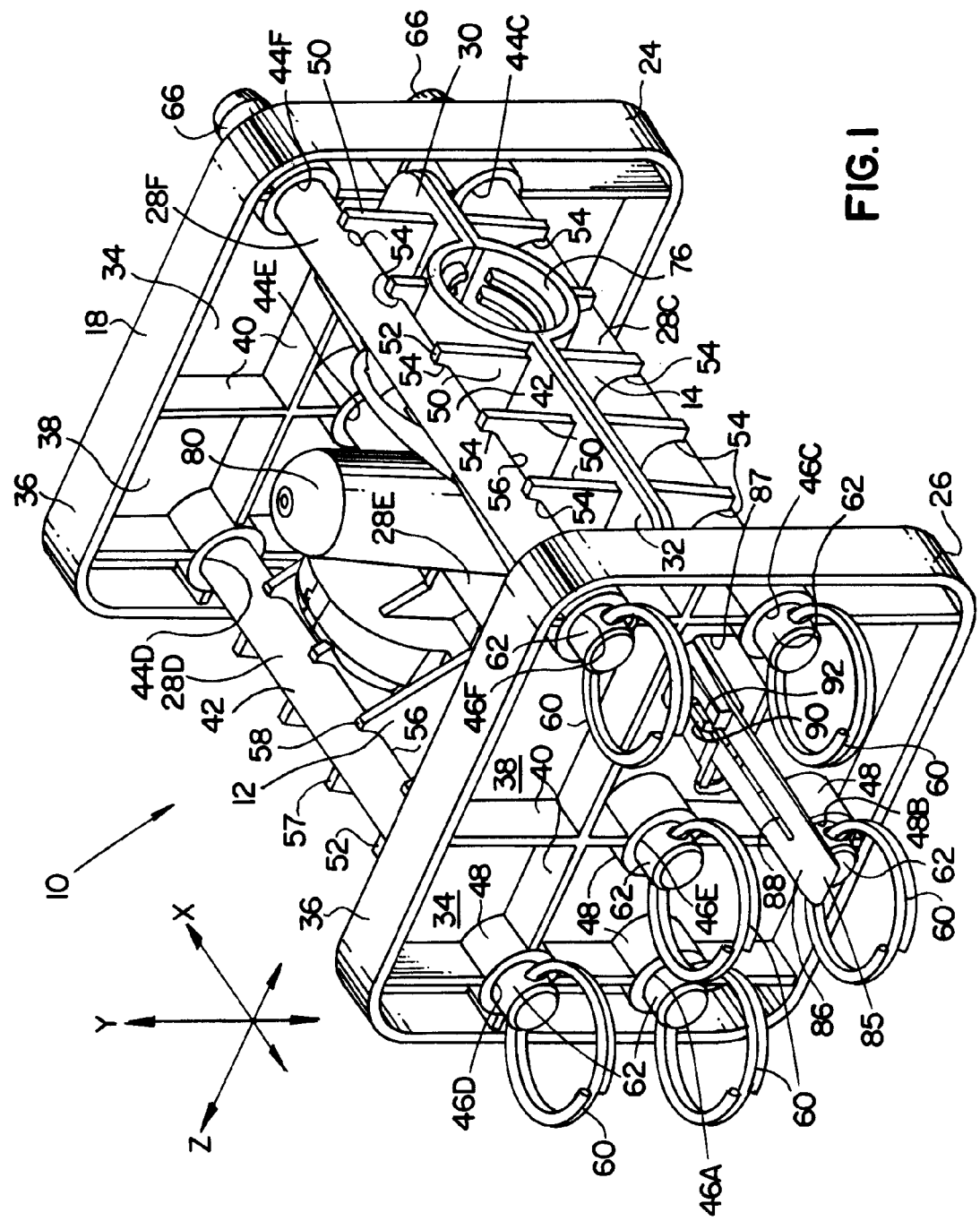
FIG. 1 is a back and right side perspective view of one form of an assembled femoral mold assembly according to the present invention.
Figure 2:
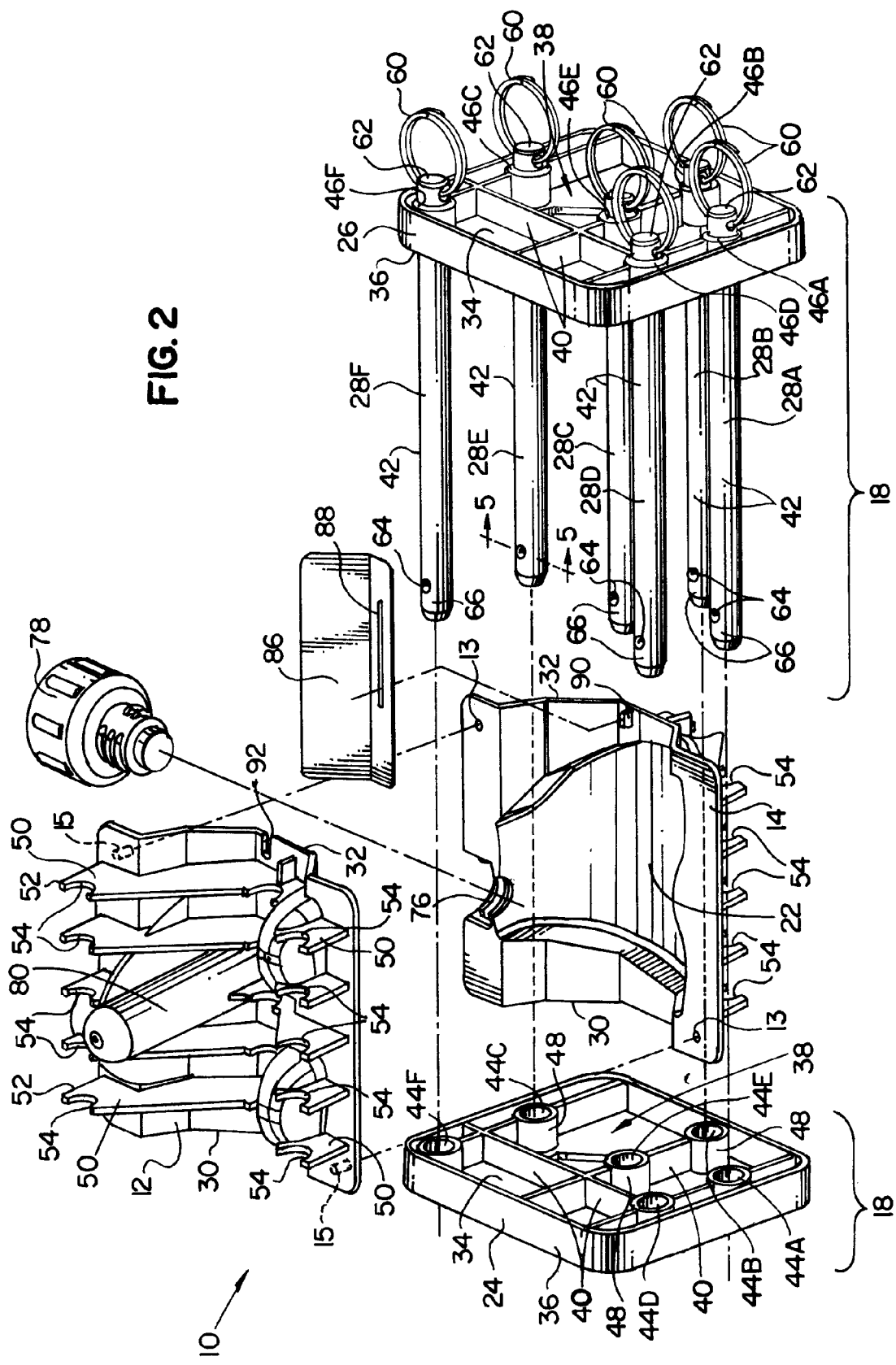
FIG. 2 is an exploded perspective view of the mold assembly of FIG. 1.
Figure 3:
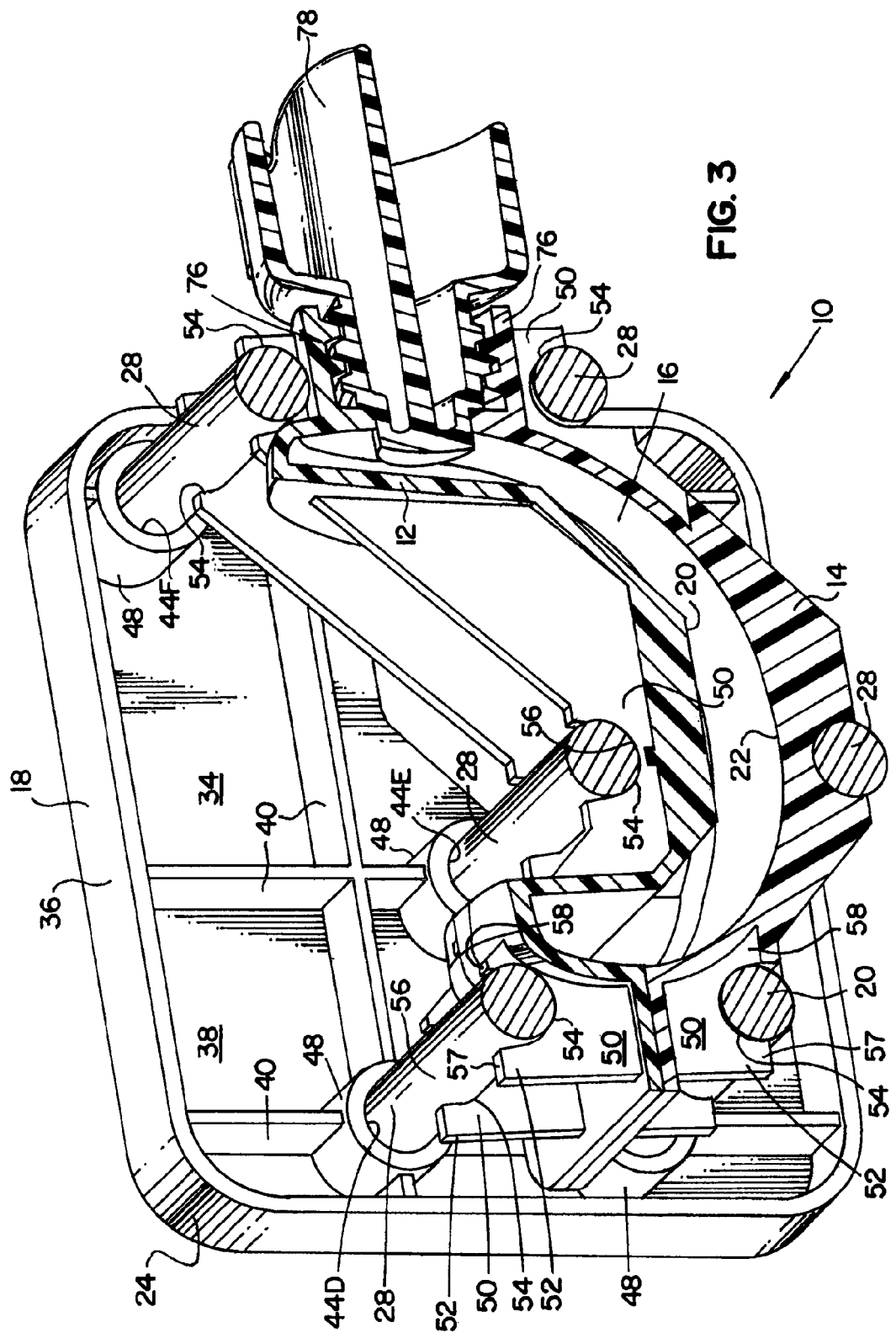
FIG. 3 is a right side cross-sectional view of the assembled mold assembly of FIG. 1.

Referring to FIGS. 1-3, a mold assembly 10 for forming a temporary prosthesis 100 (shown in FIG. 4) has at least two mold members 12 and 14 that define a generally enclosed interior cavity 16 for forming the temporary prosthesis 100. Mold members 12 and 14 may be provided in a number of different alternative sizes to form implants to match the size of a patient's anatomy, such as a knee joint. In one form, the mold assembly 10 is provided in at least four different alternative sizes when the implant 100 is a femoral knee implant, such as 66×57.5 mm, 70×61.5 mm, 74.5×65 mm, and 79×70.5 mm, where the first value relates to the size in the medial/lateral direction and the second value relates to the size in the anterior/posterior direction. The pieces of the mold assembly 10 for forming the different sizes may be provided together in a kit so that the physician can select the proper size mold pieces while the implant site is open. To provide even greater flexibility, the mold assembly 10 is configured to provide the option of a stemmed implant or a non-stemmed implant which can be decided during the surgical procedure as explained below.

Additionally, the mold members 12 and 14 can also form femoral knee implants that are configured to be placed on a specific leg, i.e., a left leg implant or a right leg implant, for each mold size to provide even greater adaptability for the physician while providing a temporary implant that better fits either the natural or abnormal curvature of the knee joint.

Furthermore, an initially separate securement structure 18 can be detachably mounted on the mold members 12 and 14 for securing the mold members 12 and 14 to each other while the interior cavity 16 (FIG. 3) is being filled with a pressurized, curable material to form the temporary prosthesis 100 in the cavity 16. The securement structure 18 can be easily and quickly mounted on, and removed from, the mold members 12 and 14 without the use of a tool providing the physician with a very convenient, quick, and clean system for forming temporary spacer implants while the implant site is open.

In more detail, the two mold members 12 and 14 respectively form an upper mold member and a lower mold member that mate together and are secured to each other by the securement structure 18. One of the mold members 12 or 14 also has two holes 13 that receive protrusions 15 (FIG. 2) from the other of the two members 12 or 14 to index the two members to each other and to limit horizontal motion relative to each other. While the two mold members 12 and 14 are the only pieces in the illustrated example that receive curing material to form the implant, it will be understood that the mold assembly 10 may contain more than two pieces to define cavity 16.

For the illustrated example, as shown on FIG. 3, the two mold members 12 and 14 respectively have interior and opposite surfaces 20 and 22 that define cavity 16. The surfaces 20 and 22 are shaped to form a femoral knee implant 100 as shown on FIG. 4 with an articulating, rounded main portion 102 to be mounted on a tibial implant, a lateral condyle 104 and a medial condyle 106 that both generally extend anteriorly from the main body 102, a posterior flange 108, and an optional stem portion 110 extending superiorly from the main portion 102 for insertion into a medullary canal on the patient's femur to anchor the implant 100 on the bone. The distal end portions of the implant's condyles 104 and 106 and the posterior flange 108 generally extend in a superior-inferior. The interior surfaces 20 and 22 respectively form a superior, bone-engaging surface 118 of the implant 100 and an inferior articulating surface 120 for engaging a tibial implant.

In order to remove the temporary implant 100 from the cavity 16 after it is formed or cured, the two mold members 12 and 14 are at least partially separable from one another. Thus, while the illustrated mold members 12 and 14 are depicted as completely separate pieces, it will be understood that the two pieces may be integrally formed. In that case, the two mold members 12 and 14 may be attached to each other by a living hinge or other similar integral and flexible structure, or the two mold members 12 and 14 may only have certain portions that can be bent back or torn away to expose implant 100 in cavity 16 for its removal therefrom.

In one form, the securement structure 18 includes at least two frame members 24 and 26 disposed on different sides of the two mold members 12 and 14, and at least one locking member (although six locking members 28A-28F are shown here) interconnecting the two frame members 24 and 26. In the illustrated form, the two frame members 24 and 26 are disposed on opposite sides 30 and 32 (such as the left and right sides) of the mold members 12 and 14 so that the locking members 28A-28F extend generally parallel in a left-to-right direction across the mold members 12 and 14. It will be appreciated, however, that while the frame members 24 and 26 are placed on the left and right sides 30 and 32 (or lateral and medial sides relative the shape of the implant the molds 12 and 14 will form), the frame members 24 and 26 could be placed on the anterior/posterior or superior/inferior sides of the implant instead. Otherwise, the frame members 24 and 26 may be placed on any sides of the mold members that are spaced from each other.

In the illustrated form, the locking members 28A-28F restrict further separation of the frame members 24 and 26 from each other. So interconnected, the frame members 24 and 26 restrict separation of the two mold members 12 and 14 from each other in a left-right, or 'x' direction as shown on FIG. 1 and indicated by the Cartesian scale. The frame members 24 and 26 restrict such motion by the mold members 12 and 14 because the mold members are disposed between the frame members 24 and 26.

The frame members 24 and 26 have a generally identical construction in the illustrated form with a generally flat main wall 34 and an outer rim 36 that extends laterally from the main wall 34; the main wall 34 and outer rim 36 generally defining an interior 38 of the frame members 24 and 26. A number of crossing flanges 40 extend in the interior 38 from the main wall 34 with the same thickness as the outer rim 36. When the mold assembly 10 is assembled, the frame members 24 and 26 both face the same direction so that one side 30 or 32 of the mold members 12 and 14 faces, and is pressed against, the main wall 34 on one of the frame members 24 or 26, while the other side 30 or 32 of the mold members 12 and 14 faces, and is pressed against, the flanges 40 on the other frame member 24 or 26.

The non-threaded locking members 28A-28F have elongate members 42, such as a pin, bar, or rod or other member that extends across the mold members 12 and 14. The left frame member 24 has at least one through-hole, but here six through-holes 44A-44F to match the number of locking members 28A-28F. Likewise, the right frame member 26 has through-holes 46A-46F that align with, or more specifically are generally coaxial with, the through-holes 44A-44F to form pairs of aligned holes to receive one of the locking members 28A-28F. For example, through-holes 44A and 46A respectively on frame members 24 and 26 are generally coaxial to receive the locking member 28A. For both of the frame members 24 and 26, the through-holes are defined by the main wall 34 and collars 48 extending interiorly from the main wall 34.

With the locking members 28A-28F assembled to the frame members 24 and 26, at least two of the locking members extend generally parallel to each other on different sides (here upper and lower sides) of the two mold members 12 and 14. In the illustrated form, three of the locking members 28A-28C extend below lower mold member 14 while the other three locking members 28D-28F extend above the upper mold member 12. With this configuration where the mold members 12 and 14 are disposed between the locking members 28A-28F, the locking members further restrict separation of the mold members 12 and 14 away from each other in an up-down or 'y' direction as shown in FIG. 1.

To restrict movement of the mold members 12 and 14 in the front-back or 'z' direction, the two mold members 12 and 14 have an array of exteriorly extending flanges 50 each with an outer edge 52 defining a recess 54. The recesses 54 are aligned to receive the locking members 28A-28F in order to mount the locking members 28A-28F on the mold assemblies 12 and 14. In one form, the recesses 54 are semicircular to flushly receive a cylindrical surface 56, for example, of each of the locking members 28A-28F.

Whether or not the recesses 54 are semi-circular, the outer edges 52 may have forward and rear portions 57 and 58 that define the recesses 54 to be sufficiently deep so that the forward and rear portions 57 and 58 extend along a sufficient height of front and back sides of the locking members 28A-28F respectively to retain the locking members 28A-28F between the forward and rear portions 56 and 58. This in turn restricts movement of the mold assemblies 12 and 14 relative to the locking members 28A-28F in the 'z' direction. Thus, in the illustrated form, the locking members 28A-28F limit the motion of the mold members 12 and 14 in at least two directions perpendicular to one another, such as in the z and y directions while the locking members 12 and 14 interconnect the frame members 24 and 26 to restrict motion of the mold members 12 and 14 in the 'x' direction. Note, however, that other forms are contemplated where such structure is not necessarily perpendicular (e.g., the locking members extend at a non-normal angle from the frame members) or the pieces of the securement structure 18 mentioned above are on different sides of the mold members than that mentioned.

Other configurations for the exterior of the mold members 12 and 14 to hold the locking members are also contemplated. For instance, instead of multiple flanges 50, one or more elongate or continuous grooves may be provided on the exterior of the mold members 12 and 14 for receiving the locking members 28A-28F. Also, instead of open recesses 54, the mold assemblies 12 and 14 may define laterally extending bores for the locking members to extend through.

The locking members 28A-28F are disposed on the mold members 12 and 14 so that moving the locking members 28A-28F axially through the through-holes 44A-44F and 46A-46F on the frame members 24 and 26 and in the recesses 54 on the mold assemblies 12 and 14 can secure and unsecure the two frame members 24 and 26 to each other, and in turn the mold members 12 and 14 to and from one another. To facilitate this securing and unsecuring action, at least one of the locking members 28A-28F, and in the illustrated form, all of the locking members 28A-28F, has a hand-operated, quick release mechanism instead of a threaded connection that may require a screw driver or may be time consuming to rotate until released. Such threading may also be difficult to release if cement becomes lodged in the threads.

For this purpose, the locking members 28A-28F each has an axially fixed finger pull ring 60 mounted at one end 62 of the locking members 28A-28F both to provide assistance in removal of the locking members 28A-28F from the frames 24 and 26, and to act as a retainer to restrict further insertion of the locking pins 28A-28F through the through-holes 44A-44F and 46A-46F. For this purpose, the outer diameter of the pull rings 60 must be greater than the inner diameter of at least the through-holes 46A-46F on the frame member 26 that directly faces the pull rings 60. The pull rings 60 may be any material that has sufficient strength to withstand being gripped and pulled by a user and being impacted by the frame member 26 caused by pressurized material filling the mold pieces. In the present form, the rings 60 are metal but may be made of plastic.

Figure 5:
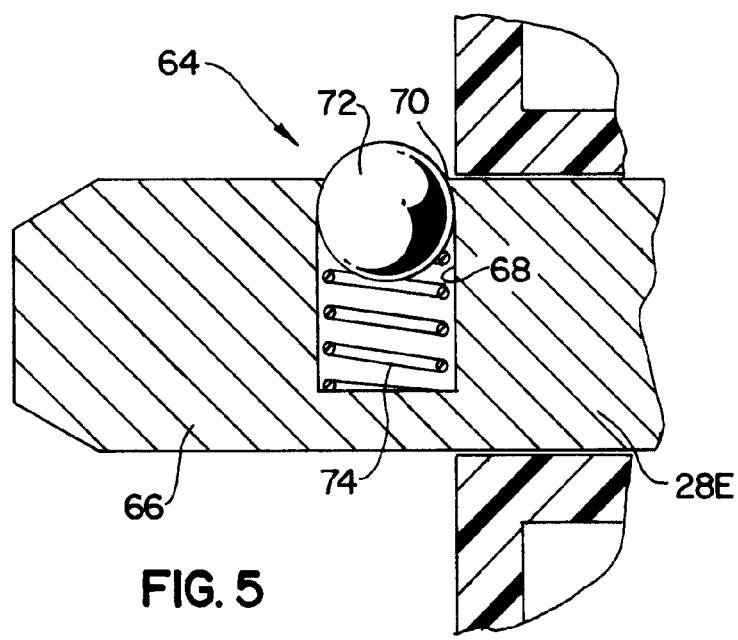
FIG. 5. a cross-sectional view of a locking member taken along line V-V on FIG. 2.

Referring to FIG. 5, the locking members 28A-28F each have a retractable retainer 64, such as a ball detent, on an end portion 66 spaced from the end 62 of the locking members 28A-28F. While the pull rings 60 are disposed at the exterior of one of the frame members 24 or 26, the retractable retainer 64 is disposed at the exterior of the other frame member 24 or 26. In the present form, the ball detent 64 includes an axially extending bore 68 with an opening 70 that is smaller than an outer diameter of a ball 72 disposed within the bore 68. The ball is biased to extend out of the bore 68 and through the opening 70 by a spring 74 also disposed within the bore. Other similar configurations may also be used as long as a retractable protrusion extends radially from the side of the locking member 28 to retain the frame member 24 when the frame member is forced outward due to forces from pressurized material filling the cavity 16, and the protrusion retracts upon a significant axial force on the locking member to intentionally disengage the locking member from the frame member.

With the configuration described, the fixed and retractable retainers 60 and 64 axially and removably fix the locking members 28A-28F to the frame members 24 and 26 while the mold is being filled with pressurized cement, and until a user pulls on the pull rings 60 to remove the locking members 28A-28F from the frame members 24 and 26 after the implant has cured. This combined structure of the frame members 24 and 26 and locking members 28A-28F provides sufficient strength to hold the mold members 12 and 14 together while receiving high pressures exhibited during injection of a curable material into the mold 10.

Referring to FIG. 3, to receive the pressurized, curable material, the mold members 12 and 14 cooperatively form an internally-threaded port 76 that receives a threaded nozzle of a cement injection gun, such as Zimmer's Power-Flo® Bone Cement Injector. While the injected, curable material is setting in the cavity 16, a plug 78 or other type of insert can be provided to close the port 76 after the curable material has been injected. Once the cavity 16 is filled, the plug 78 limits substantial amounts of curable material from leaking out of the mold assembly 10 through the port 76 so that the mold assembly 10 may be set down in any convenient orientation without adversely affecting the shape of the cured implant.

Figure 4:
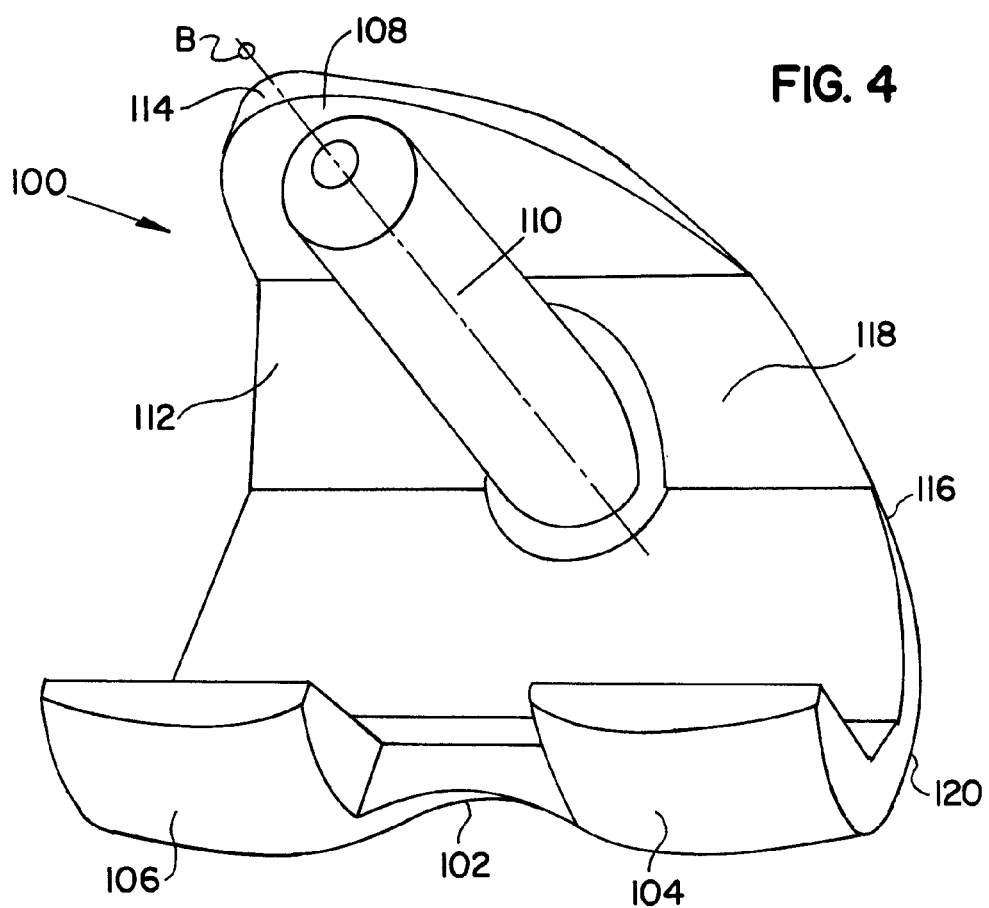
FIG. 4 is a front elevational view of a femoral implant formed with the mold assembly of FIG. 1.
Figure 6:
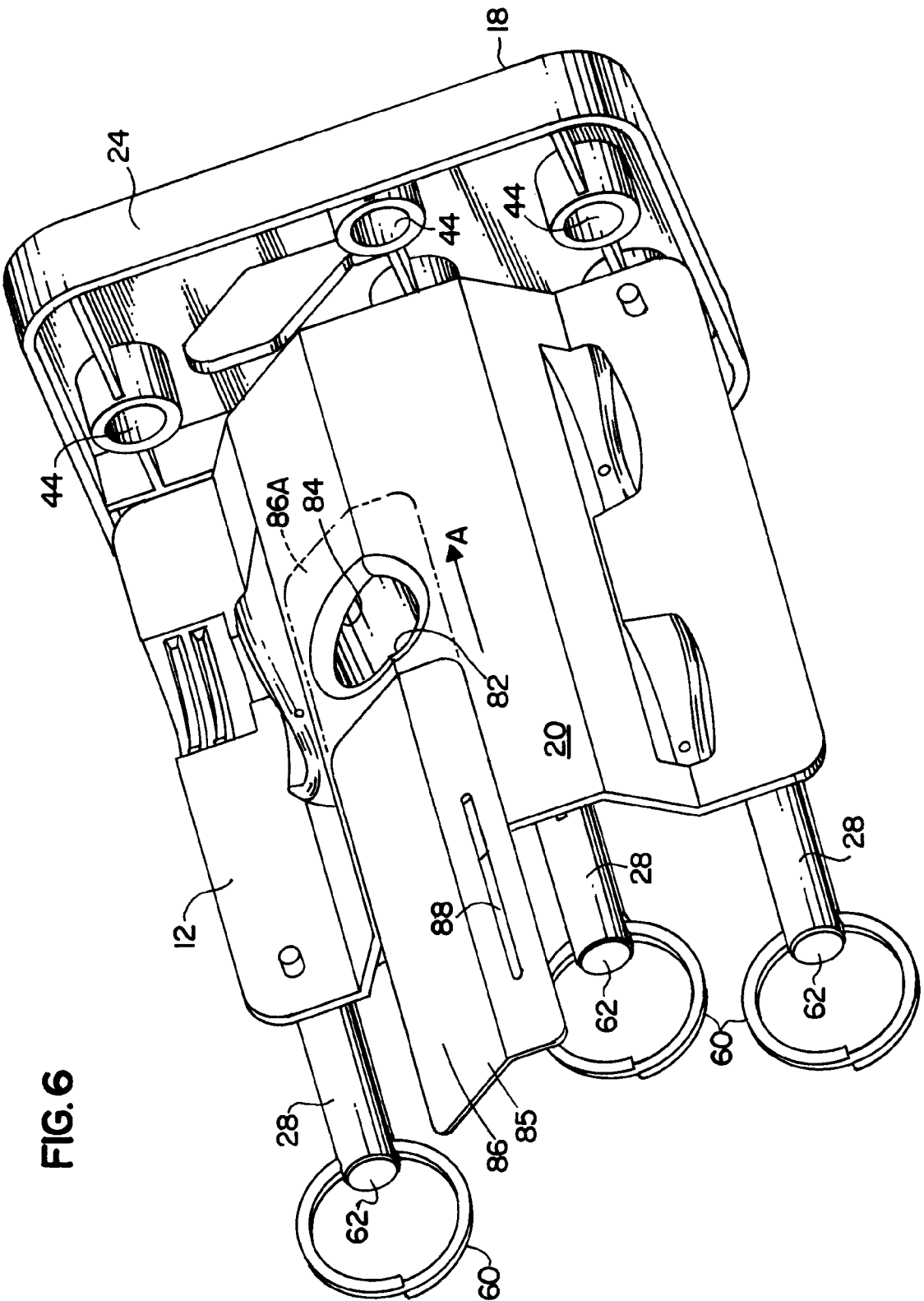
FIG. 6 is a bottom perspective view of a portion of the mold assembly of FIG. 1 showing a member in position to cover and uncover a stem-forming cavity on a mold member.

Referring to FIG. 6, in another aspect of the mold assembly 10, the mold assembly 10 can be adjustable to form the temporary prosthesis 100 either with or without the stem portion 110. To provide this option, the mold member 12 has a stem forming section 80 that defines a stem cavity 82 that is a part of the interior cavity 16. The interior surface 20 of the mold member 12 and that defines cavity 16 also defines an entrance 84 that opens to the stem cavity 82. A movable member, or slider, 86 is disposed in the interior cavity 16 and between the mold members 12 and 14. The slider 86 can be translated to cover and uncover the entrance 84. Sufficient clearance is provided between the mold members 12 and 14 at the end 32 of the mold members so that one end 85 of the slider 86 can extend out of the mold members 12 and 14 to be grasped and moved as shown in FIG. 1. The frame member 26 also has an opening 87 to provide clearance to provide access to the slider 86. The slider 86 has an elongate slot 88 generally extending in the direction it is to slide indicated by arrow 'A'. A tab or protrusion 90, also generally extending in the direction of sliding, extends on one of the mold members 12 or 14 and is disposed in the slot 88 to maintain the slider 86 on a straight alignment over the entrance 84. The other of the mold members 12 or 14 has a groove 92 (FIG. 1) to provide clearance for the tab 90 when the mold members 12 and 14 are assembled together. So configured, the slider 86 may be pushed into the mold members 12 and 14 and interior cavity 16 in the direction of arrow A as shown in FIG. 6 to the position shown in dashed line to close the entrance 84 to the stem cavity 82, which blocks cement from entering the stem cavity 82. Alternatively, the slider 86 can be pulled away from the interior cavity 16 to uncover the entrance 84 (as shown in FIG. 6) and allow for filling of the stem cavity 82 to create a stem extension 110 (FIG. 4).

Referring again to FIG. 4, the interior surfaces 20 and 22 defining cavity 16 may be shaped to form the temporary prosthesis 100 to have a body 116 in either of a first shape specifically configured for placement on a left leg, as shown on FIG. 4, or a second shape specifically configured for placement on a right leg. Thus, the stem portion 110 may be formed with a valgus angle, such as a six degree valgus angle, so that a central axis B of the stem portion 110 is generally inclined toward a medial side 112 of the implant 100. Furthermore, the implant 100 may be shaped so that a distal, superior tip 114 of the posterior flange 108 is disposed on the medial side 112 of the implant 100.

With the description as set forth above, it will be understood that mold assembly 10 is convenient to use and provides a physician with many options during the surgical procedure. The mold assemblies may be provided to the physician in a fully assembled state or may be assembled by the physician especially when the physician is choosing which size mold pieces to use, which may occur while the implant site is accessible. The entire mold assembly 10 may be provided in different sizes or alternatively a securement structure 18 may be adaptable to receive mold members 12 and 14 of different sizes. As another alternative, the mold members 12 and 14 may have the same exterior size for attachment to a single securement structure 18 and only the interior surfaces 20 and 22 of alternative mold members 12 and 14 change to correspond to different implant sizes.

Likewise, the physician may determine whether or not a stem should be placed in the implant 100 while the implant site is opened. Accordingly, the slider 86 may be positioned on the mold member 12 and moved to either cover or uncover the entrance 84 to the stem cavity 82.

After positioning the slider 86, the mold members 12 and 14 are assembled together and held together by hand for instance. The locking members 28A-28F may be inserted through one frame member 26 closest to the pull rings 60 before sliding the mold members 12 and 14 between the locking members 28A-28F. The other frame member 24 may then be secured to the locking members 28A-28F and against the side of the mold members 12 and 14. Once the mold assembly 10 is securely fastened together by the securement structure 18, the curable material can be injected into the interior cavity under pressure by attaching a cement cartridge or gun to port 76. After the mold assembly is filled with the curable material, the cement gun is removed, plug 78 is placed in port 76, and mold assembly 10 then may be set down in any convenient orientation to allow the material in cavity 16 to cure inside of the mold assembly. When the temporary prosthesis has hardened, the mold assembly 10 can be disassembled by detaching the frame member 24 from the locking members 28A-28F and then sliding the locking members 28A-28F off of the mold members 12 and 14. In one alternative, the upper three locking members 28A-28C are removed first, and the mold members 12 and 14 are then removed from the securement structure 18. Many other alternatives exist. The mold members 12 and 14 can then be pulled or peeled off of the hardened prosthesis or implant 100. The implant 100 is then trimmed and ready for implantation while the mold assembly 10 may be discarded.

Referring now to FIGS. 7-13, a tibial mold assembly 200 has at least two mold members 202 and 204 that define a generally enclosed interior cavity 206 therebetween for forming a temporary, tibial spacer or prosthesis 400. As with the femoral mold assembly 10, the mold assembly 200 can be provided in a number of different alternative sizes to fit properly on patient's anatomy having different sizes. In one form, the mold 200 is provided in at least three different sizes including 66×42 mm, 74×46 mm, and 82×51 mm, where the first value relates to the size in the medial/lateral direction and the second value relates to the size in the anterior/posterior direction. Also, a stem forming portion 230 of the mold member 202 may be plugged to provide a non-stemmed implant as with the femoral implant, and an initially separate securement structure 208 removably secures the mold members 202 and 204 to each other with sufficient strength to withstand forces impacted from filling the mold assembly 200 with pressurized, curable material while also providing an easy, quick, and clean way to remove the mold assembly 200 from the implant 400 by hand, and without the use of a tool. The mold assembly 200, however, also has a mechanism for adjusting the thickness of the cavity 206, and in turn the implant 400 formed therein as explained in greater detail below.

Figure 8:
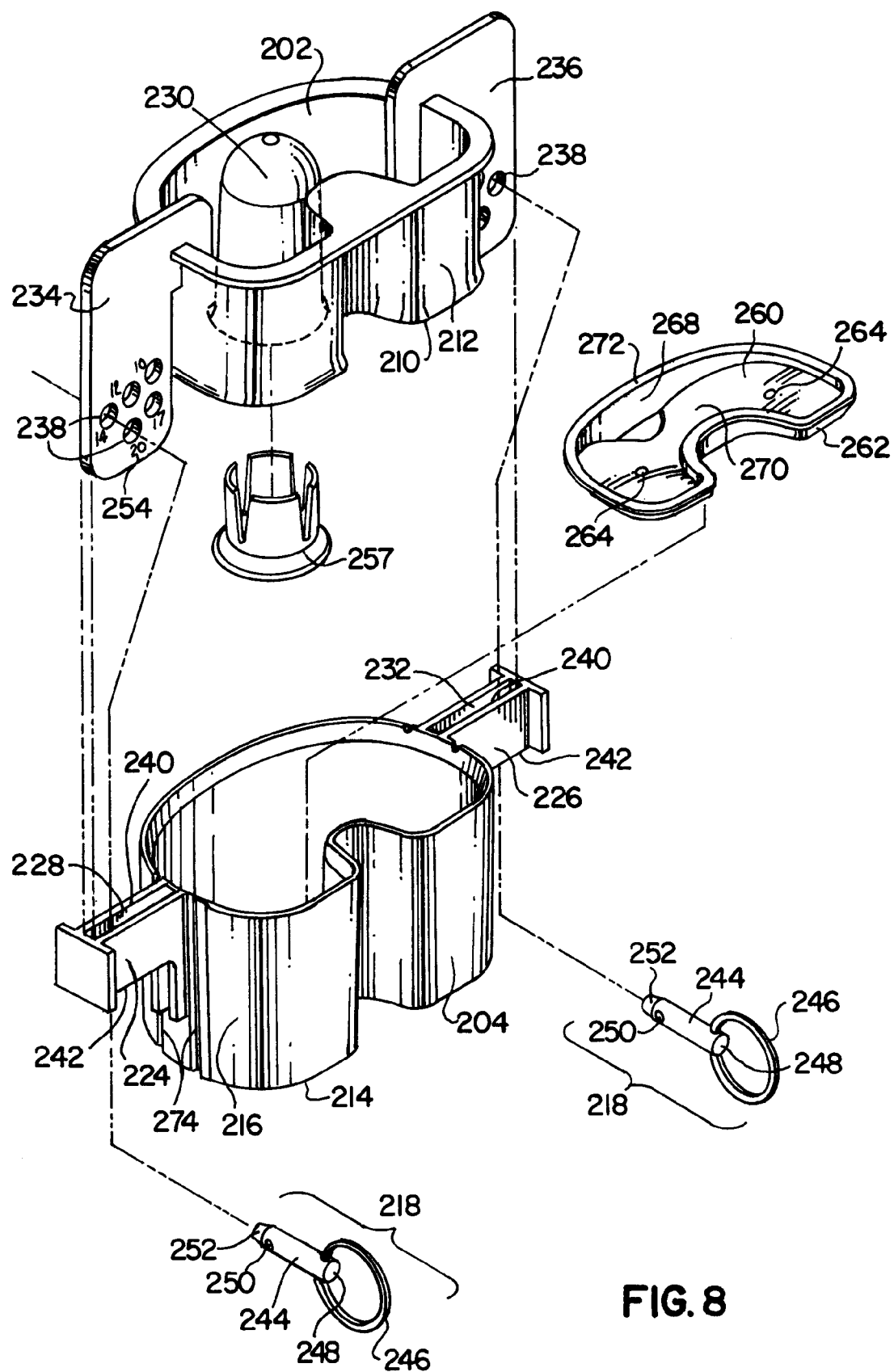
FIG. 8 is an exploded perspective view of the mold assembly of FIG. 7.
Figure 9:
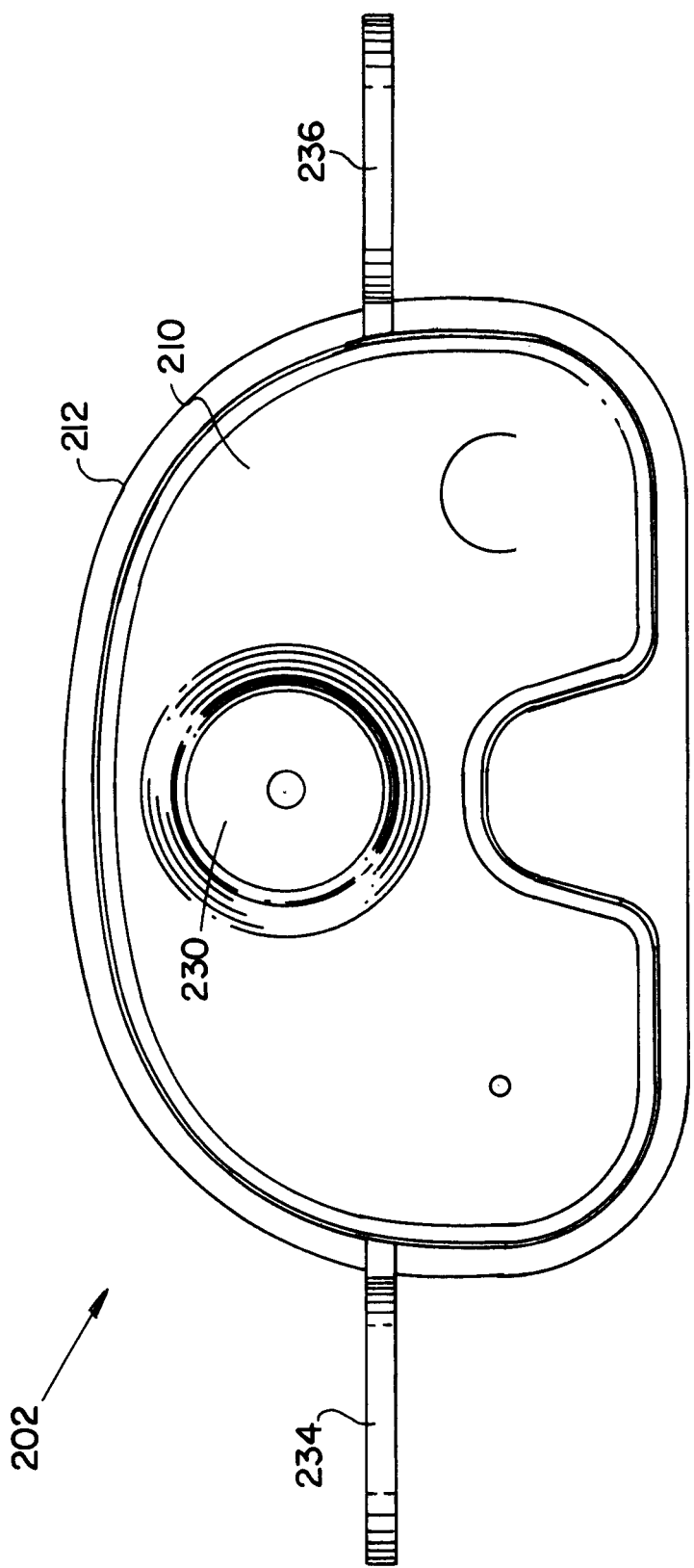
FIG. 9 is a top view of an upper mold piece of the mold assembly of FIG. 7.
Figure 10:
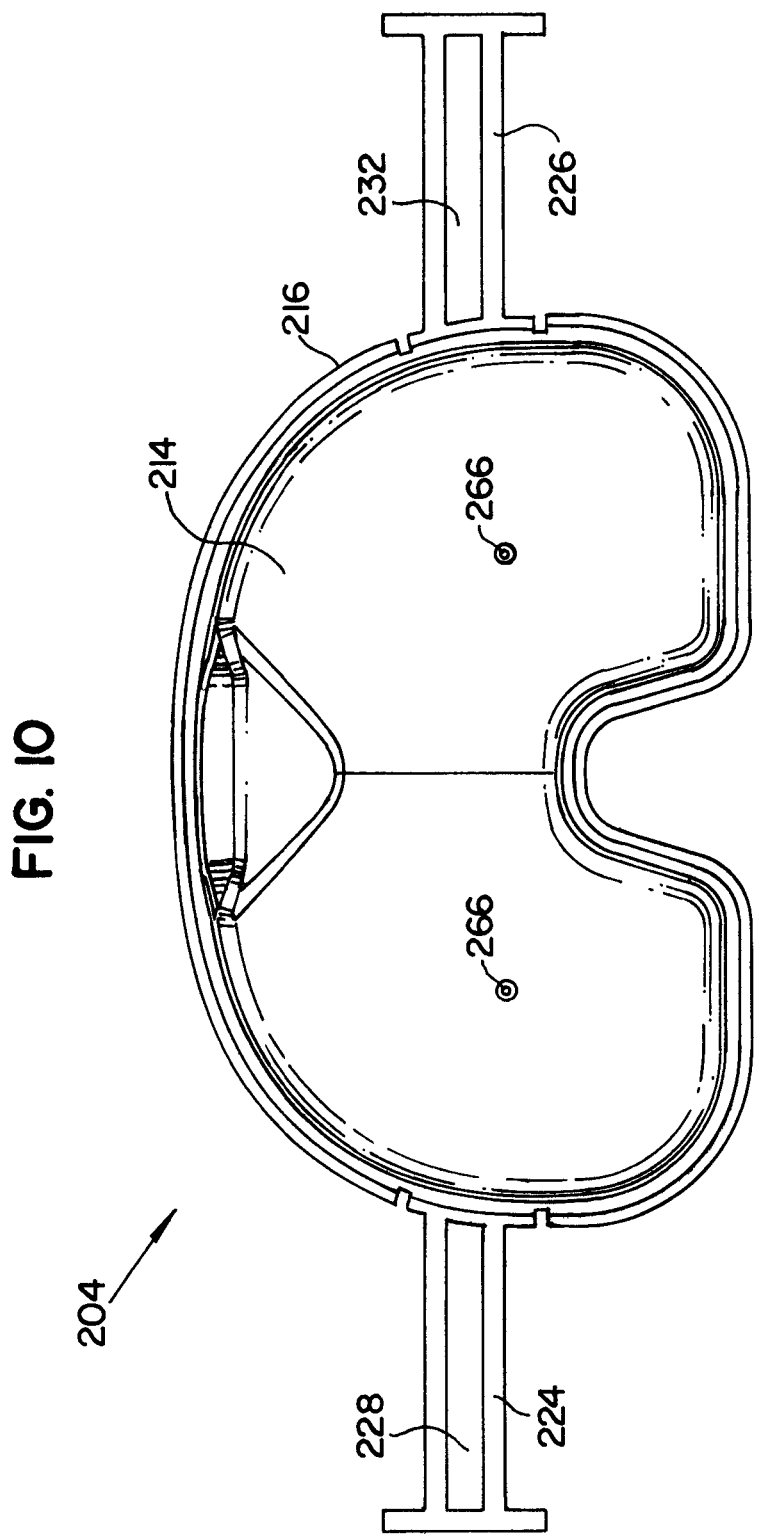
FIG. 10 is a top view of a lower mold piece of the mold assembly of FIG. 7.

As shown on FIG. 8, the mold members 202 and 204 are generally tub-shaped, and the first or upper mold member 202 is slightly smaller to fit within the second, base, or lower mold member 204. For the tibial mold assembly 200, upper and lower refers to the orientation of the mold assembly rather than the shape of the implant since the lower mold member 204 has a generally flat bottom rim that acts as a base for the mold assembly 200. Upper mold member 202 includes a bottom wall 210, and a side wall 212 extending upwardly from the bottom wall 210. Likewise, the lower mold member 204 includes a bottom wall 214 and a sidewall 216 extending upward from the bottom wall 214. The bottom wall 210 of the upper mold member 202 fits within the side wall 216 of the lower mold member 204 so that the cavity 206 is formed between the bottom walls 210 and 214. The bottom wall 210 of the upper member 202 is shaped to form the bone-engaging, inferiorly facing surface 406 of the implant 400 while the bottom wall 214 is shaped to form the superiorly facing, articulating surface 408 configured to engage a femoral implant.

Figure 11:
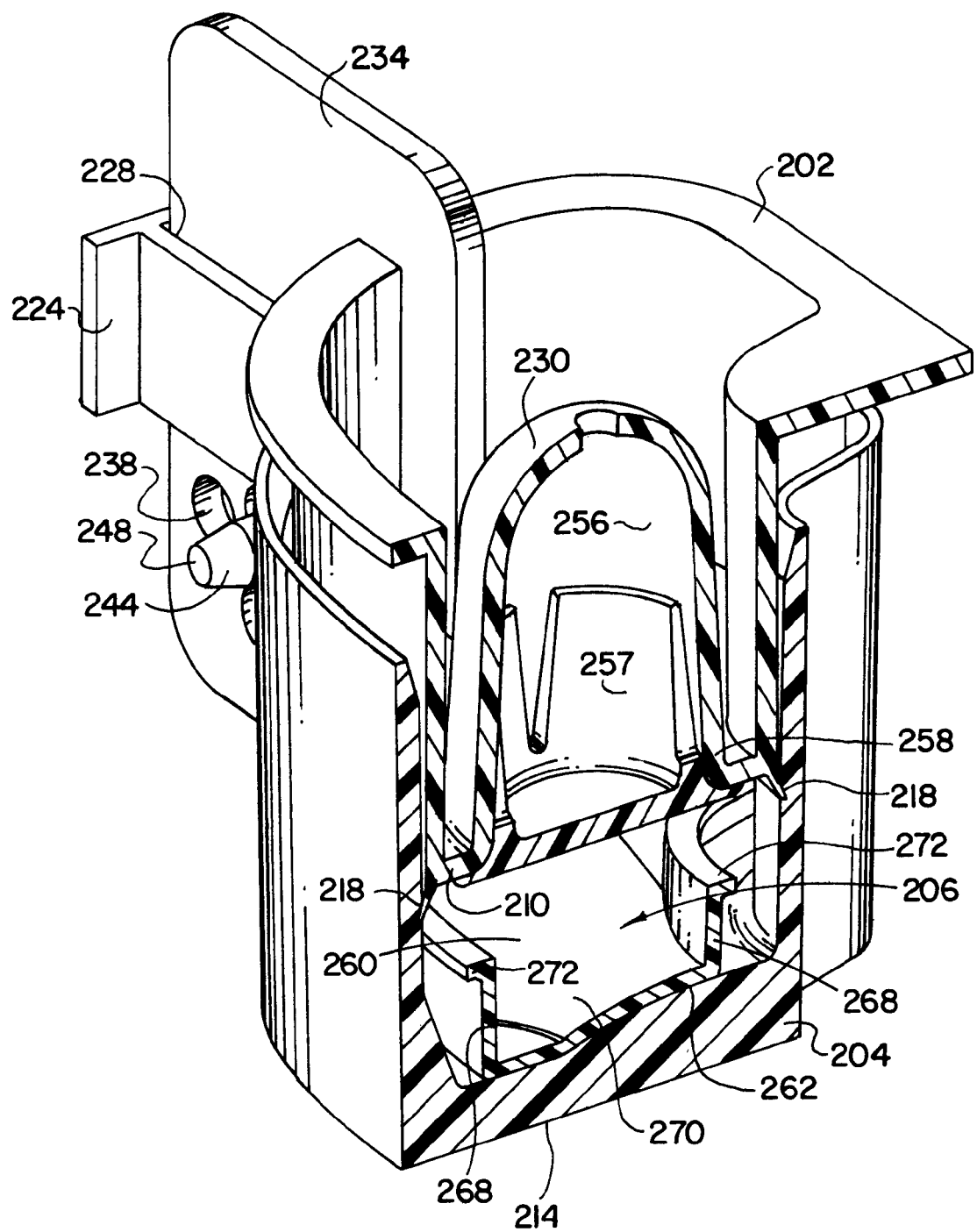
FIG. 11 is a left side, cross-sectional view of the assembled mold assembly of FIG. 7 cut through a stem portion of the mold.
Figure 12:
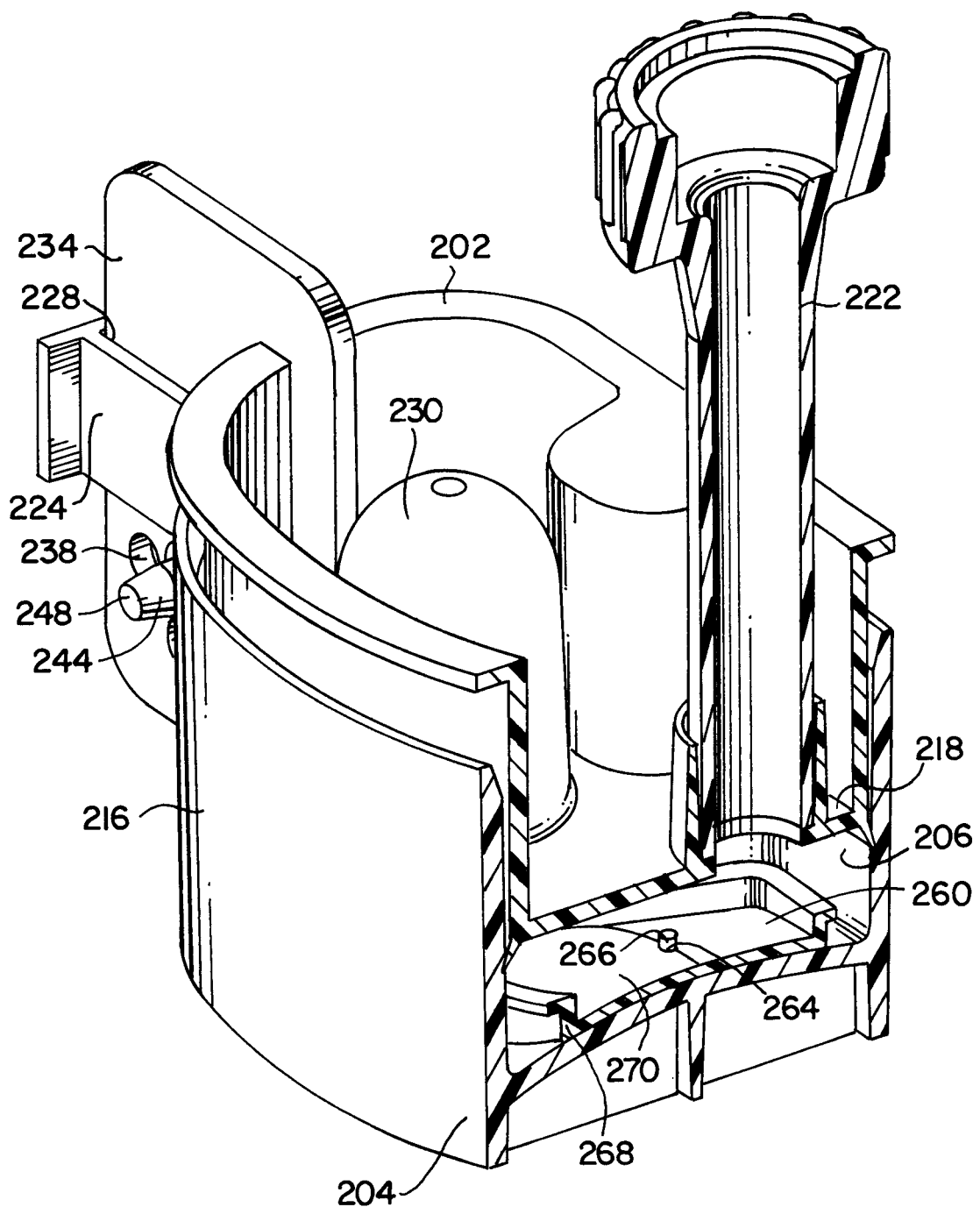
FIG. 12 is a left side cross-sectional view of the assembled mold assembly of FIG. 7 cut through a cement gun port formed on the mold assembly.
Figure 13:
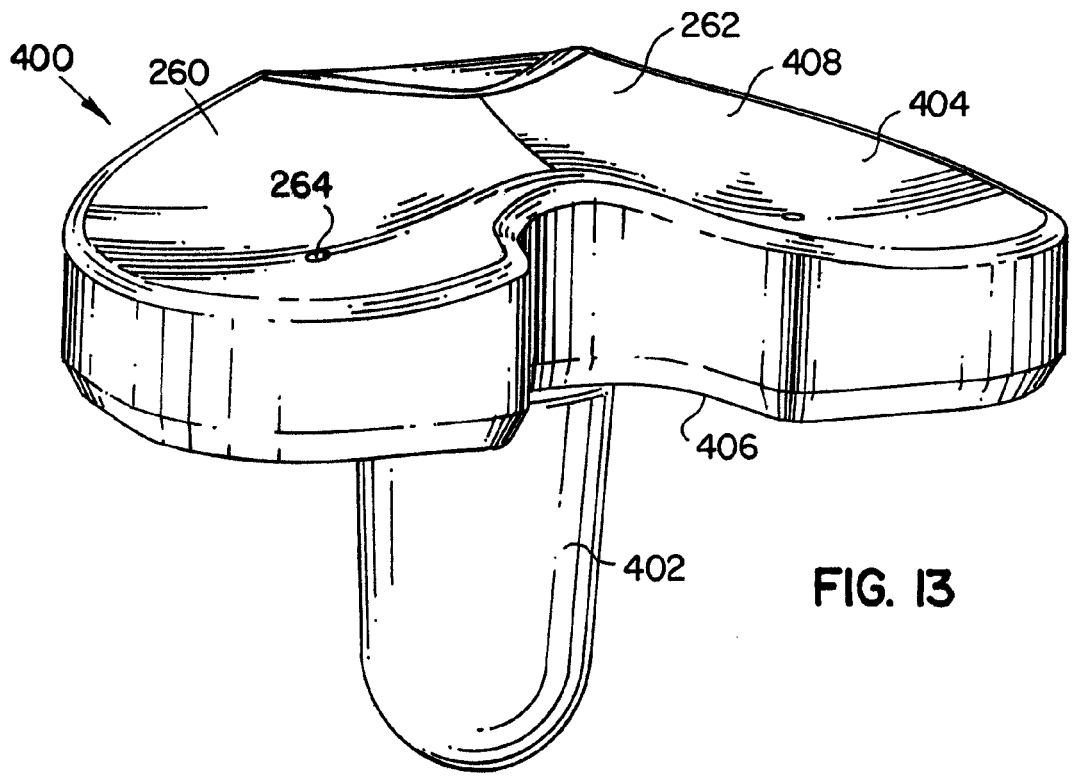
FIG. 13 is a front perspective view of the tibial implant formed by the mold assembly of FIG. 7.

Additionally, the bottom wall 210 of the upper mold member 202 may include an outwardly extending lip 218, as shown on FIG. 11, to form a tight seal with the side wall 216 of the lower mold member 204. The lip 218 limits the amount of curable material that will flow out of cavity 206 and between the sidewalls 212 and 216. The upper mold member 202 also has a stem forming section 230 extending exteriorly from the bottom wall 210 and is described in greater detail below. A port 220 is provided to inject curable material into cavity 206 and may receive a separate, long break-away nozzle 222, as shown on FIG. 12, that extends into an interior of the upper mold member 202 and attaches an injection gun or cartridge to port 220.

Figure 7:
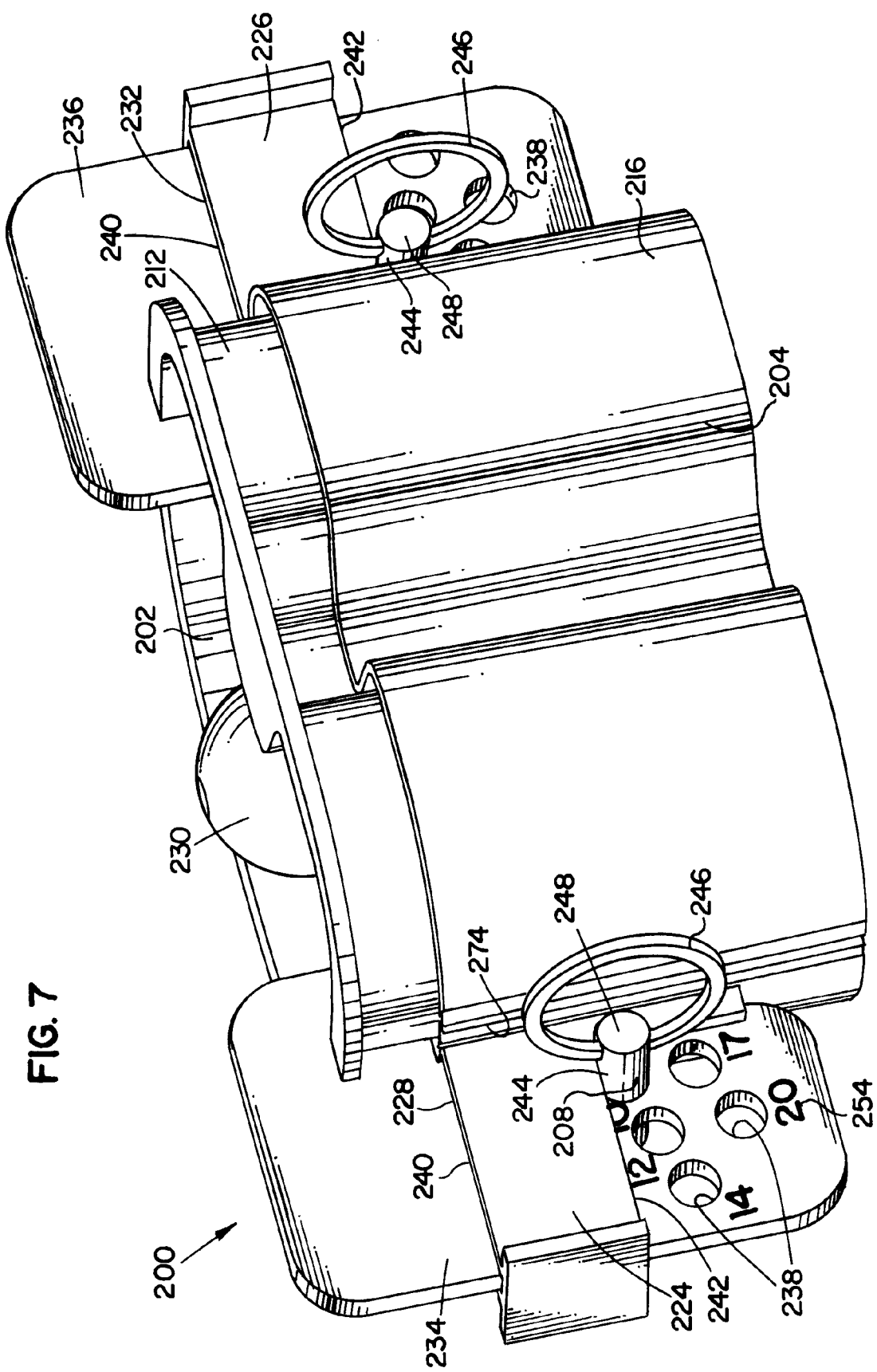
FIG. 7 is a front perspective view of one form of an assembled tibial mold assembly according to the present invention.

Referring to FIGS. 7-8, to secure the mold members 202 and 204 to each other, the lower mold member 204 has at least one, but here two, retainers in the exemplary form of arms 224 and 226 extending in opposite directions from the side wall 216. The arms 224 and 226 have a vertically accessible slot or through-opening 228 and 232 respectively. The upper mold member 202 has extensions 234 and 236 that are respectively positioned to correspond and engage the arms 224 and 226. The extensions 234 and 236 are wing or tab shaped to be inserted through the through-openings 228 and 232. Each extension 234 and 236 also has at least one hole 238 for receiving the securement structure 218 once the extensions 234 and 236 extend through the through-holes 228 and 232.

More specifically, the through-openings 228 and 232 each have an insertion side 240 and an exit side 242 through which it receives a part of the extensions 234 and 236 therethrough.

The hole or holes 238 are disposed on the extensions 234 and 236 so that once the extensions 234 and 236 extend through the arms 224 and 226, the holes 238 are disposed exteriorly of the exit side 242 of the through-openings 228 and 232. In the illustrated form, once the extensions 234 and 236 extend through the arms 224 and 226 as described, the securement structure 218, which is at least one pin 244, is placed in the holes 238 to secure the upper mold member 202 to the lower mold member 204. With this configuration, as the cavity 206 is filled with curable material, the upper upper mold member 202 will move away from the lower mold member 204. This motion will lift the extensions 234 and 236 farther out of the through-openings 228 and 232 until the pins 244 engage the retaining arms 224 and 226 of the lower mold 204. Thus, the retainers or arms 224 and 226 limit further motion of the pins 244 which in turn limits motion of the extensions 234 and 236 and prevents the upper mold member 202 from lifting out of the lower mold member 204, thereby securing the mold members 202 and 204 together.

To limit unintentional disengagement of the pins 244 from the holes 238, the pins may have pull rings 246 on one end portion 248 and retractable ball detents 250 on the other end portion 252 of the pins 244 as with the pins or locking members 28 on the mold assembly 10. When fully assembled, the pull rings 246 and detents 250 are disposed on opposite side of the extensions 234 and 236. The pull ring 246 also assists with removal of the pin 244 from the extension. It will be appreciated, however, that other configurations for the pin 244 are possible as long as a convenient and quick disengagement between a pin and the extension is provided.

This configuration permits the mold assembly 200 to be adjustable so that implants 400 with different superior-inferior thicknesses or heights may be provided by adjusting the height in the cavity 206 between the bottom wall 210 on the upper mold member 202 and the bottom wall 214 on the lower mold member 204. Specifically, each extension 234 and 236 has a plurality of holes 238 where each hole on an extension 234 and 236 has a different vertical position relative to the bottom wall 214 of the lower mold member, and therefore corresponds to a different height within the cavity 206. Since the engagement of the pins 244 with the extensions 234 and 236 forms the maximum height at which the upper mold member 202 will lift away from the lower mold member 204, the maximum height between the bottom walls 210 and 214 can be selected by inserting the pins 244 in holes 238 on extensions 234 and 236 that correspond to the desired implant height. Indicia 254 may be provided near each hole 238 on each extension 234 and 236 to indicate the implant height that will be attained by placing the pins 244 in those holes 238. In the illustrated form, five holes 238 are provided on each extension to provide implant 400 with alternative superior-inferior thicknesses of 10 mm, 12 mm, 14 mm, 17 mm, and 20 mm.

Referring to FIG. 11, the temporary tibial prosthesis 400 may have an optional stem portion 402 (shown on FIGS. 13-14) formed by stem forming section 230 on the upper mold member 202. The stem forming section 230 defines a stem cavity 256 that has an entrance or aperture 258 for receiving curable material. When a stem is not desired, a plug 258 can be inserted through entrance 258 and into stem cavity 256 to close the stem cavity.

Another optional aspect of the mold assembly 200 is that either the lower mold member 204 can form the entire articulating surface 408 of implant 400 out of the curable material or a bearing member insert 260 may form the articulating surface 408 of the tibial implant 400. In that case, the insert 260 is placed in the mold member 204 prior to addition of the curable material to become embedded on the implant 200. The insert 260 can be provided when a surgeon feels that a cement on cement articulation is not desirable which occurs when the articulating surfaces of both the femoral prosthesis and the tibial prosthesis are substantially made out of bone cement.

More specifically, a main portion 404 of the implant 400 is generally flat to form the tibial plateau and is generally C-shaped in plan view (see FIG. 13) to correspond to the shape of the condyles on the femoral implant which the main portion 404 will support. As shown in FIG. 8, the insert 260 generally matches the C-shape in plan view to adequately engage and support the femoral implant. When placing the insert 260 in the mold assembly 200, an exterior articulating surface 262 (FIG. 8) on the insert 260 is placed against the bottom wall 214 of the lower mold member 204. To aid in locating the insert 260 in a proper position within the mold member 204, at least one aperture (although two apertures are shown) 264 is formed on the articulating surface 262 and that corresponds to, and receives, protrusions 266 (shown in FIGS. 10 and 12) extending interiorly from bottom wall 214 of the mold member 204.

Figure 14:
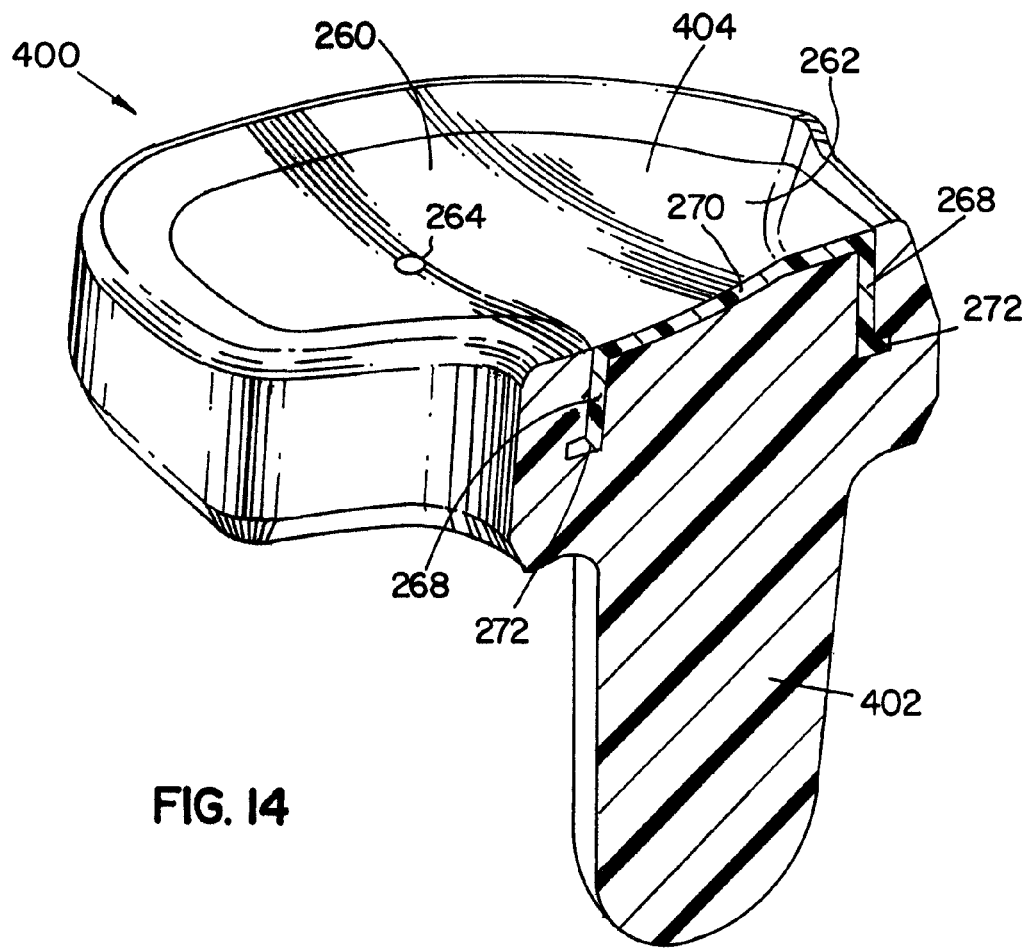
FIG. 14 is a right side cross-sectional view of the tibial implant of FIG. 12.

Referring to FIGS. 11 and 14, in order to anchor the insert 260 in the curable material, the insert 260 has a rim 268 that extends rearwardly or interiorly from a main portion 270 forming the articulating surface 262. The rim 268 has a hooked or lipped distal end portion 272 to be entirely embedded within the curable material to anchor the insert therein. So configured, once the curable material, or bone cement, is poured into the mold assembly 200, the curable material surrounds the rim 268 and distal end portion 272, and the insert 260 becomes locked into place after the bone cement cures within the mold 200.

If such cement on cement articulation is desirable, then the insert 260 would not be provided or inserted into the mold 200. In this case, the cement used in the mold member 204 may include features to form a smooth texture on the articulating surface 408 such as a fine (non-textured) finish on the mold interior surface.

For the bone engaging surface 406 of implant 400, the bottom wall 210 of the upper mold member 202 can be shaped to form a macro texture, such as large blind holes, in the bottom surface of the cured temporary prosthesis 400. These macro textures can increase the strength of the connection between the implant 400 and bone cement used as adhesive to fix the implant 400 to the tibia.

Typically the mold members 12, 14, 202 and 204 can be injection molded pieces, preferably made out of a plastic material such as a high density polyethylene or any other type of plastic that does not stick to the curable material used to form the prosthesis. Other types of mold materials may comprise hard polymers or a solid core of steel with cobalt-chromium on the exterior of the core. In one aspect, the mold assemblies 10 and 200 provide a sterile yet single-use mold assembly that is disposable after formation of the initial prosthesis. At least one or more of the mold members 12, 14, 202 and 204 can also contain a tear strip feature, such as tear strip 274 shown on FIG. 7, shaped into the mold member for assistance in disassembling of the mold after the prosthesis has cured. The tear strips can further be configured to render the molds unusable after the tear strips have been used to remove the prosthesis from the mold, thus ensuring the single-use status of the mold assembly and limiting contamination.

The mold members 12, 14, 202 and 204 in both embodiments discussed above may also contain optional vents in one or all of the mold members. The vents can allow air to escape during the injection of the curable material and can further provide a visual indicator that the mold is full, such as when the curable material begins to extrude out of the vents. The curable material that is used for the curing and forming of the temporary prosthesis can comprise a bone cement material that is typically known in the art, such as a material made out of polymethyl methacrylate (PMMA), or other similar materials. Optionally, an antimicrobial component can be added to the mixture of the curable material to provide a temporary prosthesis that has antimicrobial properties therein. Any known antimicrobial component may be utilized, and in particular, antibiotics such as gentamycin or clindamycin can be used.

In the tibial example disclosed in FIGS. 7-14, the bearing member or insert 260 can also be a plastic injection molded material, such as polyethylene or polyetheretherketone (PEEK), however, other materials may be used such as a metal insert or any other bearing surface that is desired.

As with mold assembly 10, it will be understood that mold assembly 200 also conveniently provides a physician with many options during the surgical procedure. The mold assembly 200 may be provided to the physician in a fully assembled state or may be assembled by the physician especially when the physician is choosing which size mold pieces to use and whether or not to use a stem 402 and/or a bearing insert 260 while the implant site is accessible. Accordingly, the physician may place the insert 260 in mold member 204 (or remove it therefrom) and position plug 257 in stem cavity 256 if the stem is to be omitted, all while the implant site is accessible.

To then assemble the mold assembly 200, the upper mold member 202 is placed on the lower mold member 204 so that the extensions 234 and 236 are respectively placed through arms 224 and 226. So positioned, and while the implant site is accessible as desired, the pins 244 are placed through the extensions 234 and 236 at selected holes 238 that correspond to a desired thickness or height of the implant 400 to be formed.

Once the mold assembly 200 is securely fastened together by the securement structure 208, a cement cartridge or gun is attached to the break-away nozzle 222 mounted on the port 220 to inject the curable pressurized material into the interior cavity 206. The mold assembly 200 may be set down once it is filled with the curable material. After the implant 400 is cured, the mold assembly 200 can be disassembled by detaching the pins 244, and removing the upper mold member 202 from the lower mold member 204. Tear strips 274 as mentioned above may be provided along the sides of the mold members 202 and/or 204 to assist with peeling the mold members 202 and 204 off of the implant 400.

It should be noted that all or parts of the securement structure described above could be integrally formed with the mold members. For instance, the frame members 24 and 26 on mold assembly 10 may each be integrally formed with one of the mold members 12 or 14. Likewise, mold member 204 of mold assembly 200 may have an integral pin for engaging one of multiple holes on the mold member 202.

In the presently illustrated forms, however, the non-threaded securement structures are at least partially and initially separate from the mold members in order to secure the mold members together in multiple directions (e.g., x, y, and z directions) while withstanding the relatively high forces from the pressurized curing material, and while still allowing easy disassembly of the mold members from each other. For the structures described for mold assembly 10 then, and as mentioned above, it is possible to assemble or disassemble the securement structure piece by piece. Thus, connecting the securement structure to the mold members may include mounting the mold members on a partially assembled frame, and completing the assembly of the frame to secure the two mold members together. Similarly, after the temporary prosthesis 100 or 400 is set, it is possible to detach at least a part of the securement structure from the mold members before disassembling the mold members from each other to retrieve the temporary prosthesis. Whether connecting the securement structure to the mold members or detaching at least a part of the securement structure from the mold members, this may include axially moving, by hand, at least one pin interconnecting at least two frame members disposed on different sides of the mold members.

While this invention may have been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A mold for forming a temporary prosthesis comprising:
 a first mold and a second mold being at least partially separable from each other, the first mold and the second mold defining a first enclosed interior cavity when the first mold is secured to the second mold in a first position, the first mold and the second mold defining a second enclosed interior cavity when the first mold is secured to the second mold in a second position, the second interior cavity being a different size than the first interior cavity, in the second position the entirety of one of the first and second molds is disposed in a different position relative to the other of the first and second molds than in the first position; and
 an initially separate non-threaded securement structure detachably mounted on the first mold and the second mold for securing the first mold and the second mold to each other during the forming of the temporary prosthesis, the securement structure operable to selectively secure the first mold to the second mold in the first position and the second position.

2. The mold of claim 1 wherein the securement structure secures the first mold and the second mold to each other while the mold receives pressurized, curable material for forming the temporary prosthesis.

3. The mold of claim 1 wherein the securement structure includes at least one pin disposed so that moving the at least one pin axially secures and unsecures the first mold and the second mold to and from each other.

4. The mold of claim 3 wherein the securement structure includes a finger pull ring mounted on the at least one pin.

5. The mold of claim 1 wherein the mold is adjustable to form the temporary prosthesis with or without a stem.

6. The mold of claim 1 being provided in alternative configurations wherein at least one of the first interior cavity and the second interior cavity is shaped to form the temporary prosthesis to comprise a body being provided in either of a first shape specifically configured for placement on a left leg or a second shape specifically configured for placement on a right leg.

7. The mold of claim 6 wherein at least one of the first interior cavity and the second interior cavity is shaped to provide the body with a medial side and a stem having a central axis generally inclined toward the medial side.

8. The mold of claim 6 wherein at least one of the first interior cavity and the second interior cavity is shaped to provide the body with a medial side, a main portion, and a posterior flange generally extending in a superior-inferior direction from the main portion, the flange having a distal, superior tip disposed on the medial side of the body.

9. The mold of claim 1 wherein the securement structure includes at least one pin, wherein the first mold and the second mold are secured together by the at least one pin, one of the first and second molds defining at least one hole for receiving the pin, and the other of the first and second molds having a retainer for restricting movement of the pin.

10. The mold of claim 9 wherein one of the first and second mold defines a plurality of holes for alternatively receiving the at least one pin and to define different secured positions of the second mold relative to the first mold.

11. The mold of claim 1 wherein one of the first or second mold comprises at least one extension defining at least one hole, the securement structure including a pin received within the hole, and wherein the other of the first or second mold having a retainer defining at least one through-opening for receiving the at least one extension.

12. A mold for forming a temporary prosthesis comprising:
at least two mold members being at least partially separable from each other, the at least two mold members cooperatively defining a generally enclosed interior cavity for forming the temporary prosthesis;
an initially separate non-threaded securement structure detachably mounted on the at least two mold members for securing the at least two mold members to each other during the forming of the temporary prosthesis, the securement structure being removable from the at least two mold members by hand, and without the use of a tool;
wherein the at least two mold members includes a first mold and a second mold secured together by the securement structure to cooperatively define the interior cavity therebetween, the first mold and second mold being configured to be secured at one of a plurality of alternative positions relative to each other to provide alternative dimensions for the interior cavity;
wherein one of the first or second mold comprises at least one extension defining at least one hole, the securement structure including a pin received within the hole;
wherein the other of the first or second mold having a retainer defining at least one through-opening for receiving the at least one extension, wherein the other of the first or second mold comprises a sidewall, and wherein the retainer comprises at least one arm extending from the sidewall and defining the at least one through-opening, an insertion side of the through-opening, and an exit side of the through-opening, and
wherein the at least one extension is configured to be placed through the at least one through-opening for placing the at least one hole exteriorly of the exit side of the through-opening for receiving the pin, whereby the pin retains the extension in the arm.

13. The mold of claim 1 wherein both the first mold and the second mold are generally tub shaped, wherein one of the first mold and second mold is configured to fit into the other of the first mold or second mold.

14. The mold of claim 1 wherein the first mold is configured for forming a side of the temporary prosthesis that will engage bone, the first mold having a stem forming section defining a stem cavity of the first interior cavity and the second interior cavity, the mold further comprising a plug received in the stem cavity for optionally closing the stem cavity to restrict formation of a stem on the prosthesis.

15. The mold of claim 1 further comprising a bearing member inserted into one of the first and second molds to become a part of the temporary prosthesis.

16. The mold of claim 1 wherein the temporary prosthesis is a tibial knee prosthesis and wherein multiple holes provide an adjustable superior-inferior thickness of the tibial knee prosthesis.

17. The mold of claim 1, wherein:
the first interior cavity includes:
a first cavity anterior/posterior dimension that corresponds to an anterior/posterior dimension of the temporary prosthesis;
a first cavity medial/lateral dimension that corresponds to a medial/lateral dimension of the temporary prosthesis; and
a first cavity proximal/distal dimension that corresponds to a proximal/distal dimension of the temporary prosthesis;
the second interior cavity includes:
a second cavity anterior/posterior dimension equal to the first cavity anterior/posterior dimension;
a second cavity medial/lateral dimension equal to the first cavity medial/lateral dimension; and
a second cavity proximal/distal dimension different than the first cavity proximal/distal dimension.

18. The mold of claim 12 wherein the securement structure includes a finger pull ring mounted on the pin.

19. The mold of claim 12 wherein the mold is adjustable to form the temporary prosthesis with or without a stem.

20. The mold of claim 12 wherein the extension defines a plurality of holes for alternatively receiving the pin and to define different secured positions of the second mold relative to the first mold.

21. The mold of claim 12 wherein both the first mold and the second mold are generally tub shaped, wherein one of the first mold and second mold is configured to fit into the other of the first mold or second mold.

22. The mold of claim 12 wherein the first mold is configured for forming a side of the temporary prosthesis that will engage bone, the first mold having a stem forming section defining a stem cavity of the interior cavity, the mold further comprising a plug received in the stem cavity for optionally closing the stem cavity to restrict formation of a stem on the prosthesis.

23. The mold of claim 12 further comprising a bearing member inserted into one of the first and second molds to become a part of the temporary prosthesis.

24. The mold of claim 12 wherein the temporary prosthesis is a tibial knee prosthesis and wherein multiple holes provide an adjustable superior-inferior thickness of the tibial knee prosthesis.

25. The mold of claim 12 wherein the securement structure secures the first mold and the second mold to each other while the mold receives pressurized, curable material for forming the temporary prosthesis.

* * * * *